United States Patent [19]

Fruthaler et al.

[11] Patent Number: 4,681,758
[45] Date of Patent: Jul. 21, 1987

[54] SHAPED, FLAVORED ARTICLES AND METHOD OF PRODUCING SAME

[75] Inventors: Katherine J. Fruthaler; Thomas R. Hopkins; Donald O. Hitzman; Donald H. Kubicek; Lyle R. Kallenbach, all of Bartlesville, Okla.

[73] Assignee: Phillips Petroleum Company, Bartlesville, Okla.

[21] Appl. No.: 868,921

[22] Filed: May 29, 1986

[51] Int. Cl.$^4$ .......................... A23K 1/00; C08L 89/00
[52] U.S. Cl. ...................................... 424/78; 424/499; 424/442; 424/83; 424/93; 424/410; 426/62; 426/512; 426/805; 524/17; 524/25
[58] Field of Search ....................... 424/93, 94, 78, 83, 424/14; 426/62, 805, 512; 524/17, 25

[56] References Cited

U.S. PATENT DOCUMENTS

| | | | |
|---|---|---|---|
| 2,979,778 | 4/1961 | FitzSimons | 18/58 |
| 3,119,738 | 1/1964 | Nichols | 167/53 |
| 3,166,472 | 1/1965 | Menn et al. | 167/53 |
| 3,567,119 | 3/1971 | Wilbert et al. | 239/6 |
| 3,573,924 | 4/1971 | Zarow | 99/6 |
| 3,576,760 | 4/1971 | Gould et al. | 424/50 |
| 3,650,766 | 3/1972 | Smader | 99/100 |
| 3,767,790 | 10/1973 | Guttag | 424/81 |
| 3,876,803 | 4/1975 | Stephan et al. | 426/1 |
| 3,891,759 | 6/1975 | Aries | 424/219 |
| 3,899,607 | 8/1975 | Miller et al. | 426/805 |
| 3,909,468 | 9/1975 | Tanaka et al. | 260/8 |
| 4,118,512 | 10/1978 | Eichelburg | 426/805 |
| 4,202,905 | 5/1980 | Asai et al. | 426/1 |
| 4,245,420 | 1/1981 | Carr | 43/42.06 |
| 4,344,431 | 8/1982 | Yolles | 128/260 |
| 4,361,588 | 11/1982 | Herz | 426/512 |
| 4,364,925 | 12/1982 | Fisher | 424/50 |
| 4,369,195 | 1/1983 | Nelson et al. | 426/62 |
| 4,371,562 | 2/1983 | Friedman et al. | 426/805 |

OTHER PUBLICATIONS

Chemical Marketing Reporter (Jun. 11, 1984), "Coated Lures Hook Bass".

Primary Examiner—Ronald W. Griffin
Attorney, Agent, or Firm—French & Doescher

[57] ABSTRACT

Novel articles are prepared by forming or shaping protein/polymeric material blends. The resulting articles are attractive to masticating animals. Uses for such as synthetic bones and as a bait or lure are disclosed. Novel compositions as well as method for making the novel articles of the invention are also disclosed.

21 Claims, No Drawings

SHAPED, FLAVORED ARTICLES AND METHOD OF PRODUCING SAME

This invention relates to shaped, textured articles of manufacture which have an aroma and flavor appealing to animals. In one aspect, this invention relates to a method for producing shaped, textured articles, and compositions for use in such method.

BACKGROUND

Masticating animals, such as dogs, desire solid articles on which to chew and satisfy their chewing instinct. Real bones, however, are frequently unsatisfactory because of their propensity to splinter into sharp and/or pointed pieces. Such splintered pieces can be harmful to the chewing animal. Suitable replacement articles for chewing purposes will preferably have a rugged nature suitable for chewing, a texture and appearance of a natural chewing article such as a bone, and an appealing aroma and taste to the animal.

Articles having a texture, appearance and aroma of natural food materials also find use as lures for a variety of purposes, such as, for example, fishing lures, bait for animal traps, and the like. Synthetic articles having properties appealing to the target animal, yet which are relatively inexpensive, easy to handle, and long-lasting, would find widespread utility.

OBJECTS OF THE INVENTION

An object of the present invention, therefore, is novel, shaped, flavored articles which are appealing to animals.

Another object of the present invention is a method for the production of the above-mentioned shaped, flavored articles.

These and other objects of the invention will become apparent from the disclosure and claims herein provided.

STATEMENT OF THE INVENTION

In accordance with the present invention, we have discovered that blends comprising protein-containing material and polymeric material can be subjected to conditions of temperature and pressure sufficient to raise the polymeric material to at least its melt point, forming the melt into the desired shape, then rapidly releasing the pressure to which the shaped article was subjected and allowing the article to cool. As a result of the high temperature exposure of the single cell protein material, the product article has a rich brown, beefy color and a pungent beefy aroma. Also, as a result of the rapid release of pressure as the formed product cools, a pleasing textured appearance is created on the outer surface of the article, while the inner portions of the formed article are quite porous, having a cellular structure closely resembling that of true bone. As a result of product appearance, smell and taste, the novel article of the present invention has substantial appeal to animals, as well as to the purchaser who will select such a product as a treat or feed supplement for his/her pet or domesticated animal or alternatively as bait for a species which is to be lured to a trap.

DETAILED DESCRIPTION OF THE INVENTION

In accordance with the present invention, there is provided a shaped, beefy flavored, beefy aroma article of manufacture having a textured outer surface and a porous inner structure which comprises in the range of 5 up to 50 weight percent of protein-containing material and in the range of 50 up to 95 weight percent of a polymeric material.

In accordance with another embodiment of the present invention, there is provided a method for producing a shaped, beefy flavored, beefy aroma article of manufacture having a textured outer surface and a porous inner structure which comprises:
 (a) blending a combination of
  5–50 wt. % protein-containing material, and
  50–95 wt. % polymeric material;
 (b) subjecting the blend produced in accordance with step (a) to conditions of temperature and pressure sufficient to raise the polymeric material to at least its melt point;
 (c) forming the melt produced in accordance with step (b) into a defined shape; and thereafter
 (d) rapidly releasing the pressure to which the shaped article was subjected while simultaneously allowing the article to cool.

In accordance with yet another embodiment of the present invention, there is provided a composition comprising an intimate blend of in the range of 5 up to 50 weight percent protein-containing material and in the range of 50 up to 95 weight percent polymeric material, wherein the protein-containing material has been subjected to a temperature in the range of 200° up to 400° C. for a time in the range of about 0.5 up to 120 minutes after having been blended with the polymeric material.

The novel articles of the present invention are prepared by first blending a combination of finely-divided, free-flowing, essentially dry protein-containing material and polymeric material, broadly in amounts in the range of about 5 up to 50 weight percent protein-containing material and 50 up to 95 weight percent polymeric material. Optionally, additional compounds such as medicinal compounds, growth promoting compounds, additional nutrients, flavor enhancing compounds, flavor-modifying compounds, and the like, can be included in this initial blend. Preferably, amounts in the range of about 20 up to 40 weight percent protein-containing material and 60 up to 80 weight percent polymeric material, with 25 up to 35 weight percent protein-containing material and 65 up to 75 weight percent polymeric material presently most preferred for most cost efficient use of raw materials, as well as the production of a finished article with desirable physical and sensory properties. Where additives are also employed, they will be incorporated at the relatively low levels required for their presence to be effective.

Many protein-containing materials are presently available and are useful in the practice of the present invention. Suitable protein-containing materials can be derived from plant sources, animal sources or unicellular organisms. Exemplary plant sources include soybean meal, soy protein concentrate, products derived from other seeds, alfalfa, etc. Suitable protein from unicellular organisms includes the products of algal, fungal and bacterial fermentations. Presently preferred are yeast derived single cell protein materials produced from organisms such as Torula, Pichia, Kluyveromyces, Saccharomyces, and the like. One particularly preferred single cell protein material for use in accordance with the present invention is the product of Torula yeast grown on molasses as the carbon and energy source. This is a very desirable single cell protein material for use because the final formed product has a particularly attractive beefy aroma and color appearance.

Similarly, a wide range of polymeric materials can be employed in the practice of the present invention. Broadly, those polymeric materials which can be subjected to molding or forming, employing such techniques as extrusion, i.e., polymers which flow at elevated temperatures but which possess a substantial degree of structural integrity when cooled to room temperature, are suitable. In addition, polymers employed should be either inert, i.e., nondegradable by the digestive processes of the ingesting animal, or innocuous, i.e., does not degrade to produce any components harmful to the health of the ingesting animal. Exemplary polymeric materials include food grade resins of polyolefins prepared from $C_2$–$C_{10}$ monoolefinic monomers, as well as copolymers thereof, such as, for example, polyethylene, polypropylene, and the like; monovinylarene/conjugated diene copolymers such as, for example, butadiene styrene copolymers, and the like; polyamides, such as, for example, nylon, 6,10, and the like; polyesters, such as, for example, polyvinyl acetate, polyhydroxy-$\beta$-butyric acid and the like; halogenated polyolefins, such as, for example, polyvinyl chloride-vinylidene chloride copolymers, and the like; fluorinated polyolefins such as, for example, polytetrafluoroethylene, and the like; as well as mixtures of any two or more of the above types of polymers.

Those of skill in the art recognize that additional compounds can be included in the protein-containing material/polymeric material combination, such as, for example, medicinal compounds, capable of imparting disease resistance and/or treatment to the ingesting animal; growth promoting compounds; added nutrients not provided or provided in insufficient amounts by the protein-containing component; flavor enhancing or flavor modifying components; and the like. The appealing flavor and aroma of the novel article of the present invention will facilitate delivery of the above mentioned additives to the target animal, because the animal will readily accept the article as a result of its appealing flavor, aroma and appearance. Thus, the recipient can be provided with an article that both satisfies the chewing urge, but also, to the extent the article is consumed as a result of chewing, will also provide a controlled delivery of various additives to the recipient.

Once intimately blended, the protein-containing material and polymeric material combination is then subjected to conditions of temperature and pressure sufficient to raise the polymeric material to at least its melt point. This treatment allows the protein/polymeric material blend to be formed into the shape desired for the final article. Typical conditions employed for this forming step are temperatures in the range of about 200° up to 400° C., at pressures in the range of about 1000 to 8000 psig, for contact times in the range of 0.5 up to 120 minutes.

The elevated temperatures to which the protein/polymeric material combination is subjected during the extrusion process results in a roasting or cooking of the protein-containing material, thereby darkening the protein material to a brown, meatlike color and greatly enhancing the meatlike aroma of the protein-containing material. The "meatlike aroma" of the treated material prepared in accordance with the present invention has variously been described by individuals who have inspected such material as having the aroma of barbequed chicken, fried pork rind, and the like.

As the pressure exerted on the protein/polymeric material blend during the forming or shaping operation is rapidly released and the treated article is allowed to cool, the outer surface of the formed or shaped article develops a textured appearance. The term "textured appearance" as used herein refers to the uneven surface of the article, which has a rather wavy, bumpy surface, with smooth ripples rather than a jagged unevenness. In addition, the cooled article is quite porous, having a porous, cellular structure closely resembling that of true bone. In other words, as a result of the rapid pressure drop which occurs when pressure employed during the shaping or forming process is rapidly released, the shaped or formed article "puffs" while cooling, thereby creating both the porous nature of the finished article and the puffed, rugged exterior surface of the finished article.

The shaped or formed article of the present invention is suitable for a wide range of applications. When extruded in sections of appropriate diameter, the finished article has the appearance of a doggie bone, which canines find to be quite appealing. When molded in a worm-like shape, the finished article has utility as a fishing lure. When molded or cut into appropriate shape and mounted on a mouse-trap, rat-trap or the like, the finished article has utility as bait for the animal to be entrapped. When crushed, ground, chopped, etc. into particulate matter, the composition of the present invention can be provided to animals as a component of their feed. Due to the aroma, taste and beefy appearance of the inventive articles and compositions, such particulated form can serve as a protein supplement in the animal's rations. Where additives as detailed above are included, the particulated form can serve as a means for delivery of such additives to the animal. Those of skill in the art can readily determine additional uses for which the finished articles of the present invention are suitable, the above recitation being merely suggestive and not intended to be an exclusive recitation of utility.

The following example is provided in an effort to assist one skilled in the art to a further understanding of our invention, and yet not to be unduly limitive of the reasonable scope of our invention. The particular reactants, conditions, ratios, and the like, are all intended to be illustrative of our invention, and not limitive of the reasonable and suitable scope thereof.

EXAMPLE

A blend of 30 wt. % washed, molasses-grown Torula yeast and 70 wt. % high density polyethylene pellets was prepared by tumbling the blend together as a dry mix until well mixed. The blend was then heated and extruded through a straight pipe die to produce an oval-shaped tube. The die dimensions were 1.698" by 1.938", and the extruder employed was a 2½" Hartig Extruder. An extrusion rate of 46 inches per minute was employed with a die temperature of about 150° C. (300° F.) and a pressure of about 1500 psig.

The extruded oval-shaped tube swelled upon extrusion, producing a porous, cellular structure which resembles the structure of true bone. The outer surface of the extrudate is highly textured, having a beef jerky-like appearance. The extrudate is a rich-brown color with a strong pork-rind odor.

The preceding example has been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

That which is claimed is:

1. A shaped, flavored, beefy aroma article of manufacture having a textured outer surface and a porous inner structure which comprises in the range of 5–50 wt. % of a protein-containing material and in the range of 50–95 wt. % of a polymeric material.

2. An article in accordance with claim 1 wherein said protein-containing material is selected from the group consisting of:
  soybean meal,
  soybean protein concentrate,
  protein concentrates from plant seeds,
  alfalfa,
  bacterial single cell protein material,
  fungal single cell protein material,
  algal single cell protein material,
as well as mixtures of any two or more thereof.

3. An article in accordance with claim 1 wherein said polymeric material is selected from the group consisting of:
  homopolymers or copolymers of $C_2$–$C_{10}$ monoolefins,
  monovinylarene/conjugated diene copolymers,
  polyamides,
  polyesters,
  halogenated polyolefins,
as well as mixtures of any two or more thereof.

4. An article in accordance with claim 2 wherein said fungal single cell protein material is selected from the group consisting of species of the genera:
  Pichia,
  Kluyveromyces,
  Torula,
  Saccharomyces,
as well as mixtures of any two or more thereof.

5. An article in accordance with claim 4 wherein said species of Torula is a molasses assimilating Torula species.

6. An article in accordance with claim 1 further comprising at least one compound selected from the group consisting of:
  medicinal compounds,
  growth promoting compounds,
  nutrients,
  flavor enhancing compounds,
  flavor modifying compounds,
and mixtures of any two or more thereof.

7. A method for producing a shaped, beefy flavored, beefy aroma article of manufacture having a textured outer surface and a porous inner structure which comprises:
  (a) blending a combination of
    5–50 wt. % protein-containing material, and
    50–95 wt. % polymeric material;
  (b) subjecting the blend produced in accordance with step (a) to conditions of temperature and pressure sufficient to raise the polymeric material to at least its melt point;
  (c) forming the melt produced in accordance with step (b) into a defined shape; and thereafter
  (d) rapidly releasing the pressure to which the shaped article was subjected while simultaneously allowing the article to cool.

8. A method in accordance with claim 7 wherein said protein-containing material is selected from the group consisting of:
  soybean meal,
  soybean protein concentrate,
  protein concentrates from plant seeds,
  alfalfa,
  bacterial single cell protein material,
  fungal single cell protein material,
  algal single cell protein material,
as well as mixtures of any two or more thereof.

9. A method in accordance with claim 7 wherein said polymeric material is selected from the group consisting of:
  homopolymers or copolymers of $C_2$–$C_{10}$ monoolefins,
  monovinylarene/conjugated diene copolymers,
  polyamides,
  polyesters,
  halogenated polyolefins,
  fluorinated polyolefins,
as well as mixtures of any two or more thereof.

10. A method in accordance with claim 7 wherein said fungal single cell protein material is selected from the group consisting of species of the genera:
  Pichia,
  Kluyveromyces,
  Torula,
  Saccharomyces,
as well as mixtures of any two or more thereof.

11. A method in accordance with claim 10 wherein said species of Torula is a molasses assimilating Torula species.

12. A method in accordance with claim 7 wherein said conditions of temperature and pressure comprise a temperature in the range of 200° up to 400° C. and a pressure in the range of 1000 to 5000 psig.

13. A method in accordance with claim 7 wherein said forming is accomplished by extrusion of the melt.

14. A method in accordance with claim 7 wherein said defined shape is a shape selected from the group consisting of:
  an oval-shaped tube,
  a three-dimensional block, and
  a worm-shaped tube.

15. A method in accordance with claim 7 wherein said combination further comprises at least one compound selected from the group consisting of:
  medicinal compounds,
  growth promoting compounds,
  nutrients,
  flavor enhancing compounds,
  flavor modifying compounds,
and mixtures of any two or more thereof.

16. A composition comprising an intimate blend of:
  5–50 wt. % protein-containing material, and
  50–95 wt. % polymeric material;
wherein said protein-containing material has been subjected to a temperature in the range of 200° C. up to 400° C., and a pressure in the range of 1000 to 5000 psig, for a time in the range of 0.5 up to 120 minutes after being blended with said polymeric material.

17. A composition in accordance with claim 16 wherein said protein-containing material is selected from the group consisting of:
  soybean meal,
  soybean protein concentrate,
  protein concentrates from plant seeds, alfalfa,
bacterial single cell protein material,
fungal single cell protein material,
algal single cell protein material,
as well as mixtures of any two or more thereof.

18. A composition in accordance with claim 16 wherein said polymeric material is selected from the group consisting of:
homopolymers or copolymers of $C_2$-$C_{10}$ monoolefins,
monovinylarene/conjugated diene copolymers,
polyamides,
polyesters,
halogenated polyolefins,
fluorinated polyolefins,
as well as mixtures of any two or more thereof.

19. A composition in accordance with claim 17 wherein said fungal single cell protein material is selected from the group consisting of species of the genera:
Pichia,
Kluyveromyces,
Torula,
Saccharomyces,
as well as mixtures of any two or more thereof.

20. A composition in accordance with claim 19 wherein said species of Torula is a molasses assimilating Torula species.

21. A composition in accordance with claim 16 further comprising at least one compound selected from the group consisting of:
medicinal compounds,
growth promoting compounds,
nutrients,
flavor enhancing compounds,
flavor modifying compounds,
and mixtures of any two or more thereof.

* * * * *